(12) United States Patent
Najarian et al.

(10) Patent No.: US 8,762,308 B2
(45) Date of Patent: Jun. 24, 2014

(54) COMBINING PREDICTIVE CAPABILITIES OF TRANSCRANIAL DOPPLER (TCD) WITH ELECTROCARDIOGRAM (ECG) TO PREDICT HEMORRHAGIC SHOCK

(75) Inventors: Kayvan Najarian, Glen Allen, VA (US); Kevin R. Ward, Glen Allen, VA (US); Soo-Yeon Ji, Richmond, VA (US); Roya Hakimzadeh, Glen Allen, VA (US)

(73) Assignee: Virginia Commonwealth University, Richmond, VA (US)

( * ) Notice: Subject to any disclaimer, the term of this patent is extended or adjusted under 35 U.S.C. 154(b) by 449 days.

(21) Appl. No.: 13/255,549

(22) PCT Filed: Mar. 17, 2010

(86) PCT No.: PCT/US2010/027579
§ 371 (c)(1),
(2), (4) Date: Feb. 20, 2012

(87) PCT Pub. No.: WO2010/117572
PCT Pub. Date: Oct. 14, 2010

(65) Prior Publication Data
US 2012/0136224 A1    May 31, 2012

(51) Int. Cl.
*G06N 5/00*    (2006.01)
(52) U.S. Cl.
USPC .......................................................... 706/45
(58) Field of Classification Search
None
See application file for complete search history.

(56) References Cited

U.S. PATENT DOCUMENTS

| | | |
|---|---|---|
| 2002/0138014 A1 | 9/2002 | Baura et al. |
| 2006/0264775 A1 | 11/2006 | Mills et al. |
| 2008/0027341 A1 | 1/2008 | Sackner et al. |
| 2008/0287753 A1 | 11/2008 | Parlikar et al. |

OTHER PUBLICATIONS

Journee et al. "Pulse-Wave Timing Between the Cervical Carotid and Intracranial Arteries by Means of WA Velet Transform", 18th Annual International Conference of the IEEE Engineering in Medicine and Biology Society, Amsterdam 1996, pp. 1025-1026.*

* cited by examiner

*Primary Examiner* — Li-Wu Chang
(74) *Attorney, Agent, or Firm* — Whitham Curtis Christofferson & Cook, PC

(57) ABSTRACT

A real-time decision-support system predicts hemorrhagic shock of a patient by analysis of electrocardiogram (ECG) signals and transcranial Doppler (TCD) signals from the patient. These signals are subject to signal decomposition using Discrete Wavelet Transform (DWT) to sets of wavelet coefficients and selecting significant signal features. Machine learning is applied to the significant features to evaluate and classify hypovolemia severity based on the input ECG and TCD signals from the patient. The classification of blood loss severity is displayed in real-time. An extension of the decision-support system integrates Arterial Blood Pressure (ABP) signals and thoracic electrical bio-impedance (DZT) signals with the ECG and TCD signals from the patient to evaluate severity of hypovolemia.

10 Claims, 9 Drawing Sheets

COMBINING PREDICTIVE CAPABILITIES OF TRANSCRANIAL DOPPLER (TCD) WITH ELECTROCARDIOGRAM (ECG) TO PREDICT HEMORRHAGIC SHOCK

STATEMENT OF GOVERNMENT INTEREST

This invention was made under a grant from the United States Department of Defense (contract number USAMRMC 05-0033-02). The U.S. government may have certain rights under any patent granted hereon.

DESCRIPTION

BACKGROUND OF THE INVENTION

1. Field of the Invention

The present invention generally relates to assessing the severity of blood loss and predict the occurrence of hemorrhagic shock (HS) from biomedical signals and, more particularly, to combining the predictive capabilities of Transcranial Doppler (TCD) with Electrocardiogram (ECG) to predict hemorrhagic shock.

2. Background Description

Hemorrhage is the most severe factor in traumatic injuries and their critical care. Since hemorrhage can cause inadequate tissue perfusion and organ damage, a condition termed hemorrhage shock (HS) relies heavily on the early diagnosis and treatment (see, for example, C. J. Carrico, J. B. Holcomb, I. H. Chaudry, and PULSE trauma work group (Post Resuscitative and Initial Utility of Life Saving Efforts), "Scientific priorities and strategic planning for resuscitation research and life saving therapy following traumatic injury", *Academic Emergency Medicine*, 2002, vol. 9, pp. 621-626, [2], and G. Gutierrez, H. D. Reines, and M. E. Wulf-Gutierrez, "Clinical review: Hemorrhagic shock", Critical Care, 2004, vol, 8, pp. 373-381). Classifying the degree of severity of blood loss is vital in ensuring prompt treatment and a higher survival rate. Prompt detection and treatment of hemorrhagic injuries is also essential in the military field and for civilian trauma patients. Therefore, it is highly desirable to evaluate the severity of blood loss and predict the future occurrence of hemorrhagic shock (HS) by processing biomedical signals available in clinical settings.

Biological time series recognition analysis has been studied for many years to obtain significant information associated with diseases. For example, Electrocardiography (ECG) analysis has been shown to provide abnormal heart function information about autonomic control of the cardiovascular system, and so can explain a variety of cardiac dysfunctions (see, for example, Task Force of the European Society of Cardiology and the North American Society of Pacing and Electrophysiology, "Heart rate variability: standards of measurement, physiological interpretation and clinical use", *Circulation*, 1996, vol. 93, pp. 1043-1065). By analyzing the physiological signal, an early diagnosis may be obtained. Even though, ECG combined with blood pressure (BP) is useful for analyzing cardiac activity, it may be insufficient for early estimation of hemorrhagic shock (see, for example, C. C. Wo, W. C. Shoemaker, P. L. Appel, M. H. Bishop, H. B. Kram, and E. Hardin, "Unreliability of blood pressure and heart rate to evaluate cardiac output in emergency resuscitation and critical illness", *Critical Care Medicine*, 1993, vol. 21, pp. 218-223, S. A. Stern, S. C. Dronen, P. Birrer, X. Wang, "Effect of blood pressure on hemorrhage volume and survival in a near-fatal hemorrhage model incorporating a vascular injury", *Annals of Emergency Medicine*, 1993, vol. 22, no. 2, pp. 155-63, and D. G. Newman, R. Callister, "The non-invasive assessment of stroke volume and cardiac output by impedance cardiography review", *Aviation, Space, and Environmental Medicine*, 1999, vol. 70, pp. 780-789). Incorporating other physiological signals may therefore further improve such estimations.

Transcranial Doppler (TCD) ultrasound is a non-invasive medical monitoring method that is clinically used to examine the circulation of blood inside the human brain. During a typical TCD monitoring, ultrasound waves, which are transmitted through the tissues inside the skull, are reflected off the red blood cells moving along the blood vessels. Detection of these echoes allows estimation of the blood flow. The real-time use of TCD monitoring can also be used to monitor and record the blood flow inside the brain during a number of important surgical procedures. Measurement of blood flow can be used to assess flow deficits and to guide therapeutic interventions directed at optimizing cerebral blood flow (see, for example, V. L. Babikian, L. R. Wechsler, *Transcranial Doppler Ultrasonography*, Butterworth-Heinemann, Boston, 1999, and B. Bein, P. Meybohm, E. Cavus, P. H. Tonner, M. Steinfath, J. Scholz, and V. Doerges, "A comparison of transcranial Doppler with near infrared spectroscopy and indocyanine green during hemorrhagic shock: a prospective experimental study", *Critical Care*, vol. 10, no. 1, 2006).

Many physiological time series are non-stationary, as they show very irregular and complex time-varying statistical patterns. Analyses of physiological signals commonly use Fourier transformation (FT). FT is known to be suitable for extracting frequency information from signals. However, it has a clear disadvantage when using non-stationary signal such as ECG and TCD and does not provide time information from the signal (see, for example, Task Force of the European Society of Cardiology and the North American Society of Pacing and Electrophysiology, "Heart rate variability: standards of measurement, physiological interpretation and clinical use", *Circulation*, vol. 93, pp. 1043-1065, 1996). In particular, when time information has valuable knowledge such as HS due to assess the rapid change of response in hemorrhage; the FT cannot help to extract the time information. Therefore, wavelet transformation (WT) (see, for example, Mallat, A., *Wavelet Tour of Signal Processing*, Academic Press, San Diego, USA, 1998, R. M. Rao and A. S. Bopardikar, *Wavelet Transforms Introduction to Theory and Applications*, Addison Wesley Ed. 1998, C. S. Burrus, R. A. Gopinath, and H. Guo, *Introduction to Wavelets and Wavelet Transforms, a Primer*, Prentice Hall Inc. 1997) is applied to obtain the time-frequency information from the TCD and ECG. Wavelet transformation is a promising technique for extracting time-frequency information which is called multi-resolution analysis. Multi-resolution wavelet analysis has been widely applied to many fields, especially to biomedical signals, such as brain wave signal processing (see, for example, M. Kawase, T. Komatsu, U. Kondo, K. Nishiwaki, T. Kimura, and Y. Shimada, "Hemorrhage exerts different effects on variability of heart rate and blood pressure in dogs", *The Japanese Journal of Anesthesiology*, vol. 47, pp. 925-932, 1998, and M. F. Hilton, R. A. Bates, K. R. Godfrey, M. J. Chappell, and R. M. Cayton, "Evaluation of frequency and time-frequency spectral analysis of heart rate variability as a diagnostic marker of the sleep apnoea syndrome", *Medical & Biological Engineering Computing*, vol. 37, pp. 760-769, 1999) and ECG analysis (see, for example, X. M. Wu, R. J. Ceng, J. D. Liang, and H. Y. Li, "The study on the principle of wavelet analysis of the heart function parameters", *Journal of Jinan University*, vol. 18, pp. 53-57, 1997).

SUMMARY OF THE INVENTION

An embodiment of the invention assesses the severity of blood loss and predict the occurrence of hemorrhagic shock (HS) from biomedical signals.

An embodiment of the invention maximizes the survival rate in cases of blood loss by predicting the occurrence of hemorrhagic shock with biomedical signals.

According to an embodiment of the invention, two types of physiological signals, Electrocardiography (ECG) and Transcranial Doppler (TCD), are used to discover the degree of severity. Transcranial Doppler (TCD) signal is used to predict and classify the degree of severity of blood loss either as mild, moderate, and severe or as severe and non-severe. Discrete wavelet transformation (DWT) is used. DWT decomposes signals at different levels with different frequencies by calculating the correlations of the signal with shifted and scaled versions of a mother wavelet. Coefficients including detail coefficients and approximate coefficients are used. In addition, ANOVA statistical analysis is performed to assess the significance of features.

One objective of the invention is to classify the severity of hemorrhage from patterns in physiological signals using discrete wavelet transformation (DWT) and machine learning. The performance of the wavelet method was tested using multiple physiological signals, and specifically ECG and TCD signals, from a model of hemorrhage in healthy conscious humans, called lower body negative pressure (LBNP). Machine learning (ML) algorithms are then applied to predict hemorrhage states i.e., mild, moderate and severe, and non-severe and severe. Thus, the invention allows assessment of volume loss and prediction of hemorrhagic shock (HS), particularly in cases of traumatic injury. It can also be used for real-time monitoring of internal bleeding during surgical procedures.

An extension of the basic embodiment integrates Arterial Blood Pressure (ABP) and thoracic electrical bio-impedance (DZT) signals with the ECG and TCD signals to provide information from all common vital signals to evaluate severity of hypovolemia.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

An embodiment of the invention is described in terms of a system on which the methods of the invention may be implemented. The system is composed of various signal processing components, databases and computational interfaces that one of ordinary skill in the computational and signal processing arts will be familiar with. The methods of the invention are described with reference to flowcharts which illustrate the logic of the processes implemented. The flowcharts and the accompanying descriptions are sufficient for one of ordinary skill in the computer programming, signal processing and image processing arts to prepare the necessary code to implement the embodiment of the invention.

Figure 1:
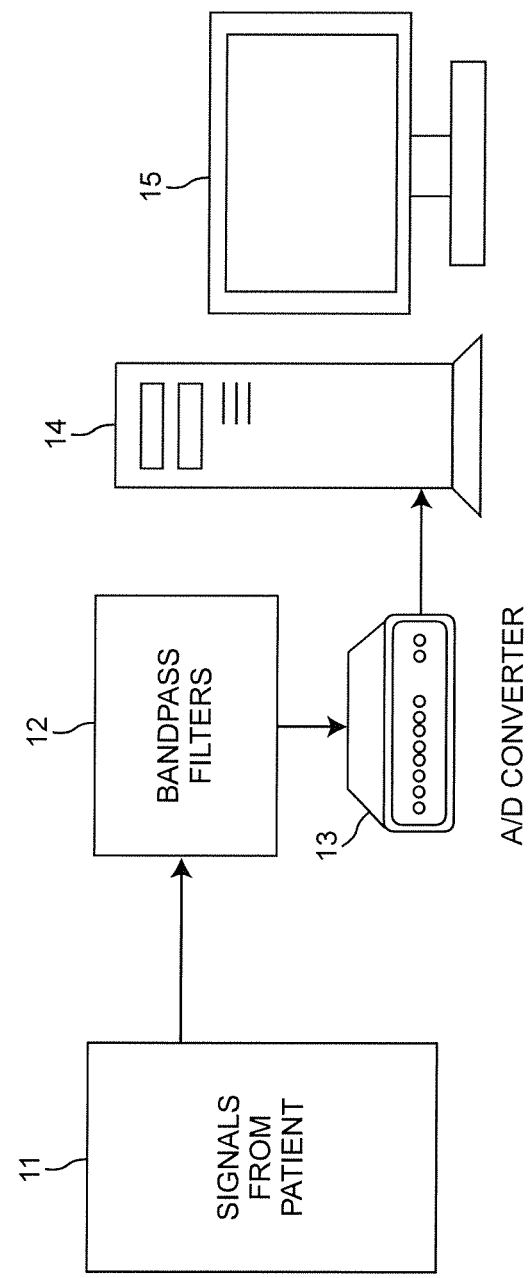
FIG. 1 is a block diagram illustrating a decision-support system on which the embodiment of the invention may be implemented.

Referring to the drawings, and more particularly to FIG. 1, there is shown a decision-support system on which the embodiment of the invention may be implemented. Signals from the patient are generated at 11. These signals include in one application Electrocardiogram (ECG) signals and Transcranial Doppler (TCD) signals. In a second application, in addition to ECG and TCD signals, arterial blood pressure (ABP) signals and thoracic electrical impedance (DZT) signals are added. These signals are filtered in bandpass filters 12 and input to data processing system 14, such as a personal computer, which provides output on display 15.

The system described encompasses two applications. The first application, Application 1, focuses on the use of a Transcranial Doppler (TCD) signal in estimating severity of hypovolemia (a state of decreased blood volume in the body). TCD measures the velocity of blood flow through the brain's blood vessels, and therefore has potential use in detecting hypovolemic shock characterized by reduced blood flow through the brain. This application uses wavelet transform to analyze the non-stationary TCD signal; unlike other techniques, wavelet transform preserves the time information in the signal, which is critical when evaluating a patient's condition and predicting the need for treatment. This application offers further improved performance by integrating electrocardiogram (ECG) signals of heart activity into the analysis. Combined, the information extracted from these two signals is used to identify the degree of blood volume loss, and can be used as part of a computerized decision support system to assist physicians in treating hypovolemic patients.

The main significance of Application 1 is:

The analysis of TCD signal via wavelet transform to detect hypovolemia severity.

The integration of TCD and ECG analysis to identify the degree of blood volume loss and provide warnings of patient condition to physicians and medical staff.

Though the second application offers higher accuracy for estimating hypovolemia, the advantage of the first application is in its use of only two signals: TCD and ECG. This requires collecting only two signals from a patient, which may be useful in cases where urgent treatment is vital or in remote settings where only limited equipment is available for use.

The second application, Application 2, presents an extension of the first application. While the first application integrates only two signals, the second application integrates all available information from a wider range of signals to provide more reliable detection of patients at high risk of hypovolemia. In addition, this application uses non-overlapping sliding windows to better capture fast changes in patient condition.

The main significance of Application 2 is:

The integration of all available information from various common vital signals, analyzed with a non-overlapping sliding window, to evaluate severity of hypovolemia. Since different signals may produce different responses at the similar level of severity, integrating them into a decision support system provides better reliability.

Figure 2:
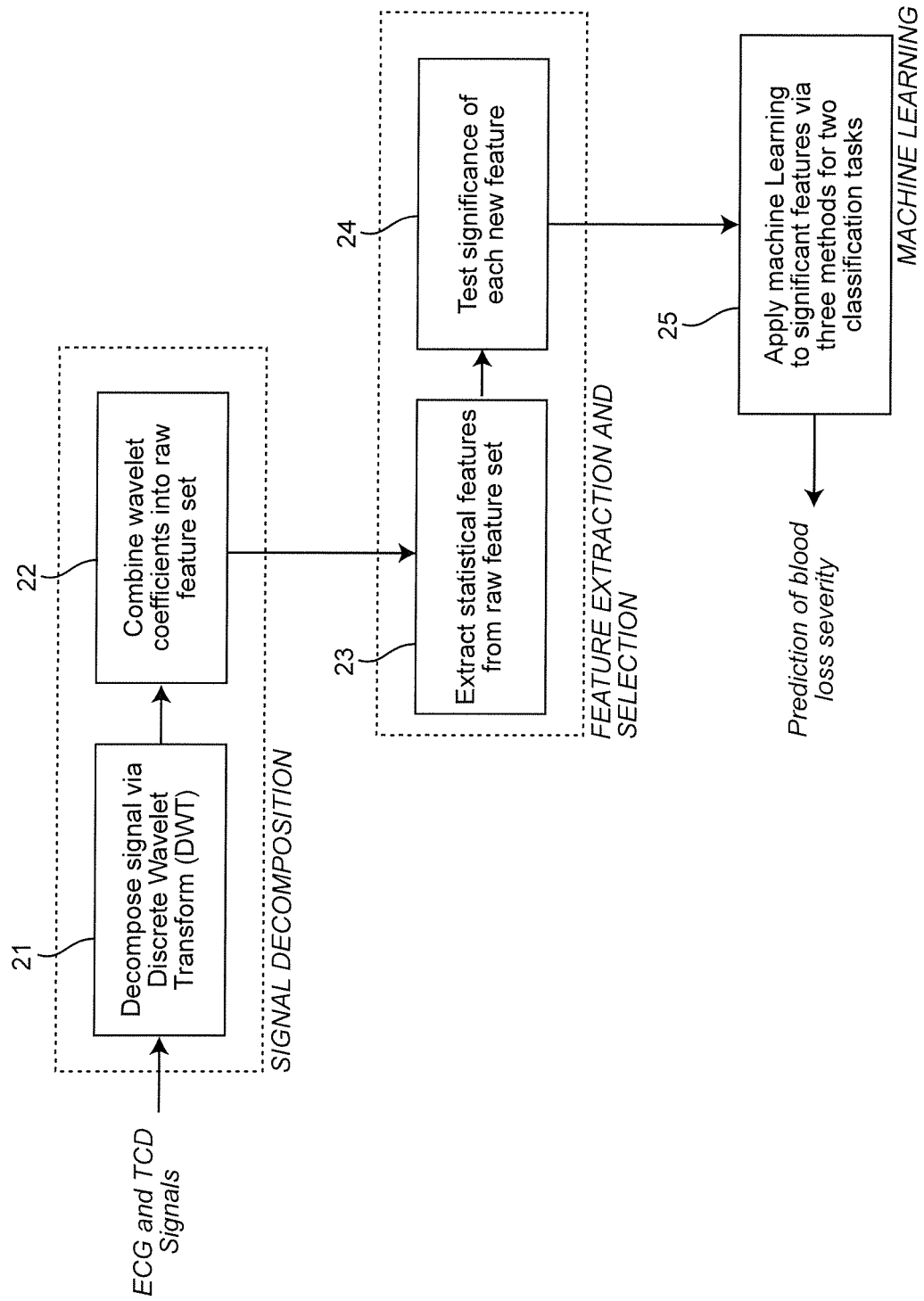
FIG. 2 is a flowchart illustrating the overall logic implemented integrating two physiological signals to detect the severity of hypovolemia.

Referring again to the drawings, and more particularly to FIG. 2, there is shown an overview of the process of integrating two physiological signals (TCD and ECG), i.e., Application 1, to detect the severity of hypovolemia. The inputs are ECG and TCD signals. The first step 21 is to decompose these signals via Discrete Wavelet Transform (DWT) to generate wavelet coefficients. In step 22, the wavelet coefficients are combined into a raw feature set. This raw feature set is then subject to feature extraction and selection. In step 23, statistical features are extracted from the raw feature set. Then, in step 24, the significance of each new feature is tested. The output of this process is input to step 25, which applies machine learning to significant features via one of three method for two classification tasks. The output is prediction of blood loss severity. This output is provided in real-time and displayed on display 15 for physicians in the decision support system shown in FIG. 1.

Figure 3:
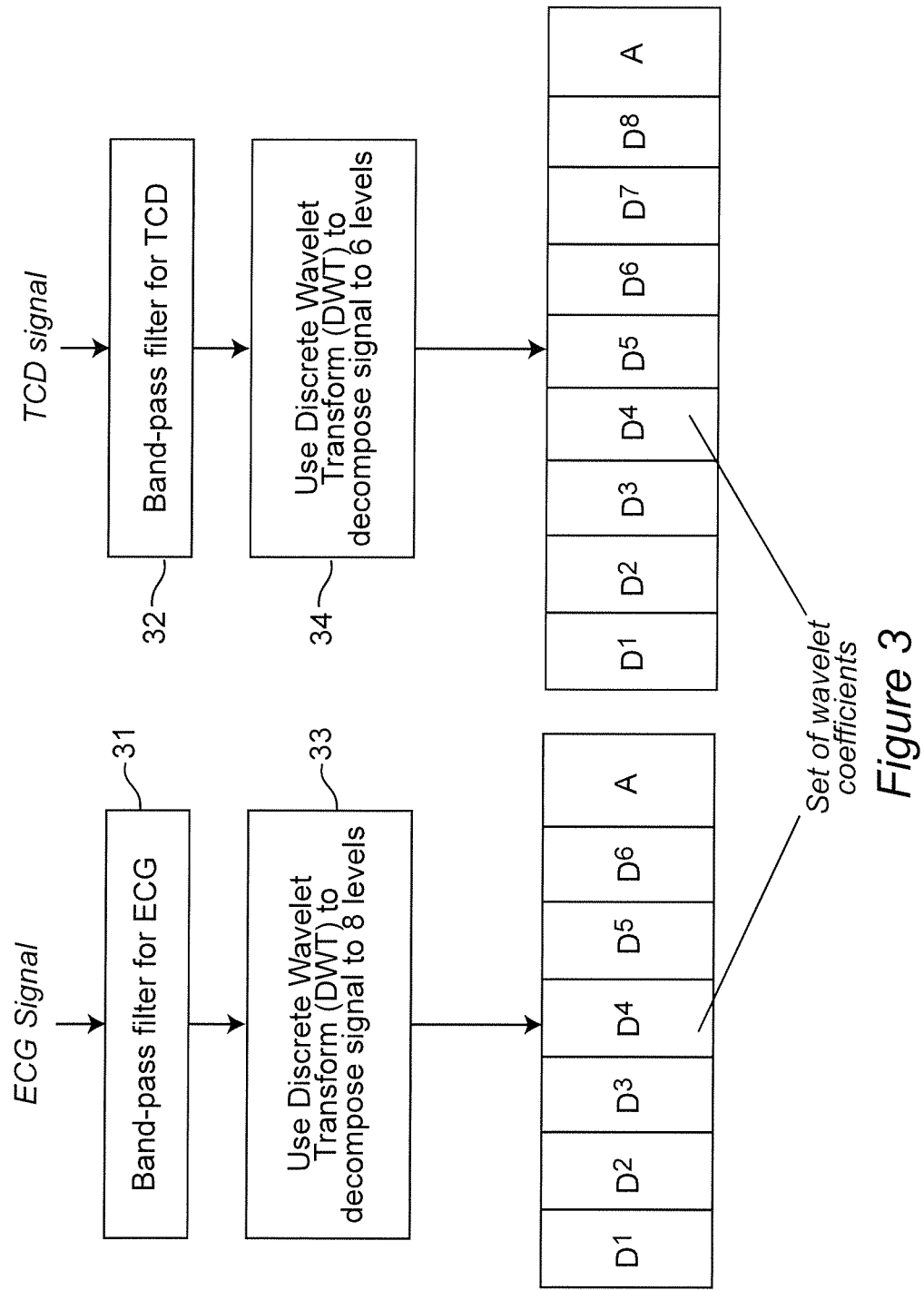
FIG. 3 is a flowchart illustrating the logic of the signal decomposition process component of the process shown in FIG. 2.

The signal decomposition stage decomposes the TCD and ECG signals into detail coefficients containing hidden information that is later used in classifying the severity of patient state. A flowchart of the process is presented in FIG. 3. The inputs to the decomposition stage input are two raw physiological signals, Transcranial Doppler (TCD) and Electrocardiogram (ECG), in numerical form. Both the TCD and ECG signals include unwanted frequencies due to subject movement and power line interference. This noise can affect the results of processing, so filtering is therefore performed as the first steps 31 and 32. An order 2 band-pass filter is applied to both signals separately. A band-pass filter takes a signal as input and a specified frequency range; frequencies of the signal within this range are passed as output, while frequencies outside are attenuated. The range is determined based on the dominant frequencies of the TCD and ECG signals.

In steps 33 and 35, the bandpassed signals are decomposed via Discrete Wavelet Transform (DWT). DWT is a common technique that is particularly useful in analyzing non-stationary signals; i.e., signals whose frequency contents change over time, such as TCD. The DWT of a signal is calculated by sending it through a multiple levels consisting of low-pass and high-pass filters. A low-pass filter smooths or approximates a signal by attenuating high frequencies. A high-pass filter does the reverse, attenuating low frequencies in order to emphasize the details contained in the higher frequencies. For a raw input signal x, the low and high pass outputs are the level 1 approximation and detail coefficients $A_1$ and $D_1$ respectively, formulated as:

$$A_1 = (x*g)\downarrow 2$$

$$D_1 = (x*h)\downarrow 2$$

where g and h are the impulse responses of the low-pass and high-pass filter respectively. Note that the filter outputs are sub-sampled by factor 2; this is because the decomposition process removes half the frequencies of the raw signal x. Although only half of each filter's output characterizes the signal, each filter's output has half the frequency band of the input, so the frequency resolution (which contains the useful information) has been doubled.

This process continues for as many levels of decomposition as specified. This stage applies eight and six levels of decomposition to the TCD and ECG signals, respectively; much of the useful information in the signal is contained in the high frequency components, and must to be extracted through multiple sets of detail coefficients. The Daubechies 4 (db4) form of DWT is used, since the db4 mother wavelet has strong similarity with P-QRS-T wave. The output of this stage for ECG is a set of detail coefficients ($D_1, D_2, D_3, D_4, D_5, D_6$) and an approximation coefficient A. The output for TCD is a set of detail coefficients ($D_1, D_2, D_3, D_4, D_5, D_6, D_7, D_8$) and an approximation coefficient A. More detail on DWT can be found in "A Review of Wavelets in Biomedical Applications" (Michael Unser and Akram Aldroubi, Proceedings of the IEEE, vol. 84, no. 4, pp. 626-638, April 1996). (See also, Y. Meyer, *Wavelets: Algorithms and Application*, SIAM, Philadelphia, 1993; M. Unser and A. Aldroubi, "A review of wavelets in biomedical applications", *Proceedings of the IEEE*, 84(4):626-638, 1996; P. S. Addison, "Wavelet Transforms and the ECG: A review", *Physiological Measurement*, 26:R155-R199, 2005; and A. Aldroubi and M. A. Unser, *Wavelets in Medicine and Biology*, CRC Press, 1996.)

Figure 4:
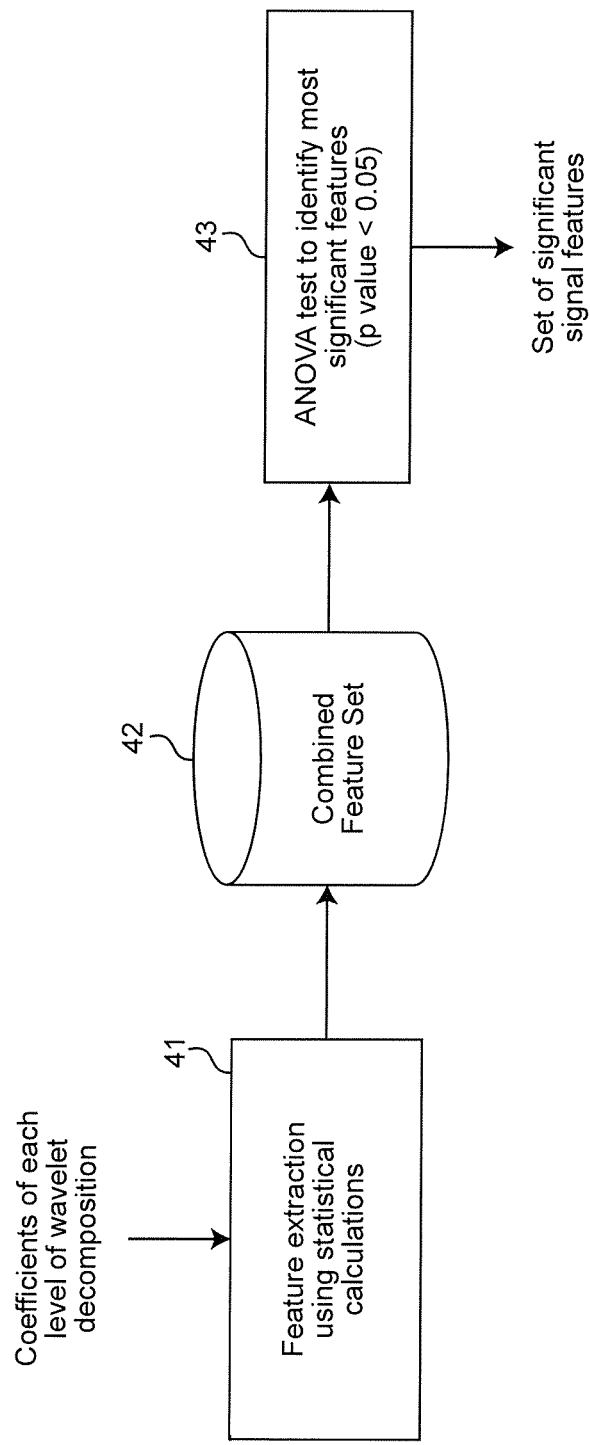
FIG. 4 is a flowchart illustrating the logic of the feature extraction and selection component of the process shown in FIG. 2.

The outputs of the signal decomposition stage are, for ECG, a set of six detail coefficients and the approximation coefficient; and for TCD, a set of eight detail coefficients and the approximation coefficient. These are applied to the feature extraction and selection stage. This stage extracts quantitative features from the wavelet coefficients generated in the signal decomposition stage, and selects the most statistically significant of these for severity classification. A flowchart illustrating the feature extraction and selection process is presented in FIG. 4. The output of this stage is the set of significant features that can be shown the hidden pattern of the signals.

In step 41, feature extraction using statistical calculations is performed. The wavelet coefficients extracted in the previous stage present the correlation between the signal and the mother wavelet in both low and high frequencies. These coefficients contain underlying knowledge in the signal, which is now extracted by calculating various quantitative features.

For ECG, level 6 decomposition was performed using the db4 wavelet. The following features are calculated:

$$D^j = \frac{1}{n}\sum_{i=1}^{n}(d_i^j)^2$$

$$A = \frac{1}{m}\sum_{i=1}^{m}(a_i)^2$$

Relative Entropy:

$$\varepsilon_i = -p\log_2 p \text{ where } p = \frac{A}{D^1 + D^2 + D^3 + D^4 + D^5 + D^6 + A}$$

$\alpha_1^J$=value immediately prior to median of 20 highest energy values from each level's detail coefficients $\alpha_2^j$=median of 20 highest energy values from each level's detail coefficients $\alpha_3^j$=value immediately after median of 20 highest energy values from each level's detail coefficients where n is the length of the detail coefficient, m is the length of the approximation coefficient, $d_i^j$ is the detail coefficient of level j and $a_i$ is the approximation coefficient.

For TCD, level 8 decomposition was performed using the db4 wavelet. The following features are calculated:

$$D^j = \frac{1}{n}\sum_{i=1}^{n}(d_i^j)^2$$

$$A = \frac{1}{m}\sum_{i=1}^{m}(a_i)^2$$

$$\text{Entropy}(D^j) = -\sum_{i=1}^{n} p_i \log_2 p_i \text{ where } p_i = \frac{d_i}{\sum_i d_i^j}$$

$$\text{Entropy}(A) = -\sum_{i=1}^{m} p_i \log_2 p_i \text{ where } p_i = \frac{a_i}{\sum_i a_i^j}$$

$$v_j = \frac{1}{n}\sum_{i=1}^{n}(d_i^j - \mu^j)^2 \text{ where } \mu^j = \frac{1}{n}\sum_{i=1}^{n} d_i^j \quad j = 1, \ldots, 8$$

$$v_a = \frac{1}{m}\sum_{i=1}^{m}(a_i - \mu_a)^2 \text{ where } \mu_a = \frac{1}{m}\sum_{i=1}^{m} a_i$$

$\alpha_1^j$=value immediately prior to median of 20 highest energy values from each level's detail coefficients $\alpha_2^j$=median of 20 highest energy values from each level's detail coefficients $\alpha_3^j$=value immediately after median of 20 highest energy values from each level's detail coefficients where n is the length of the detail coefficient, in is the length of the approximation coefficient, $d_i^j$ is the detail coefficient of level j and $a_i$ is the approximation coefficient.

In steps 42 and 43, the features are collected into a feature set and feature selection is performed. All features extracted from the wavelet coefficients are assembled into an intermediary feature set. Feature selection is then applied to select the final feature set to be used for classification. This is done via analysis of variance (ANOVA). ANOVA is a technique for analyzing experimental data which can be used to compare the means of the response variable for various combinations of the classification feature variables contained in the full feature set. Selected features are added to the final feature set if the resulting p-value is below a certain level. In this application, the value is tested at the 5% significance level, or p=0.05. This selects the features that are most informative in predicting the severity of hypovolemia, and removes those that are redundant or irrelevant (as these may not only have no use in prediction, but may actually negatively impact the accuracy).

Figure 5:
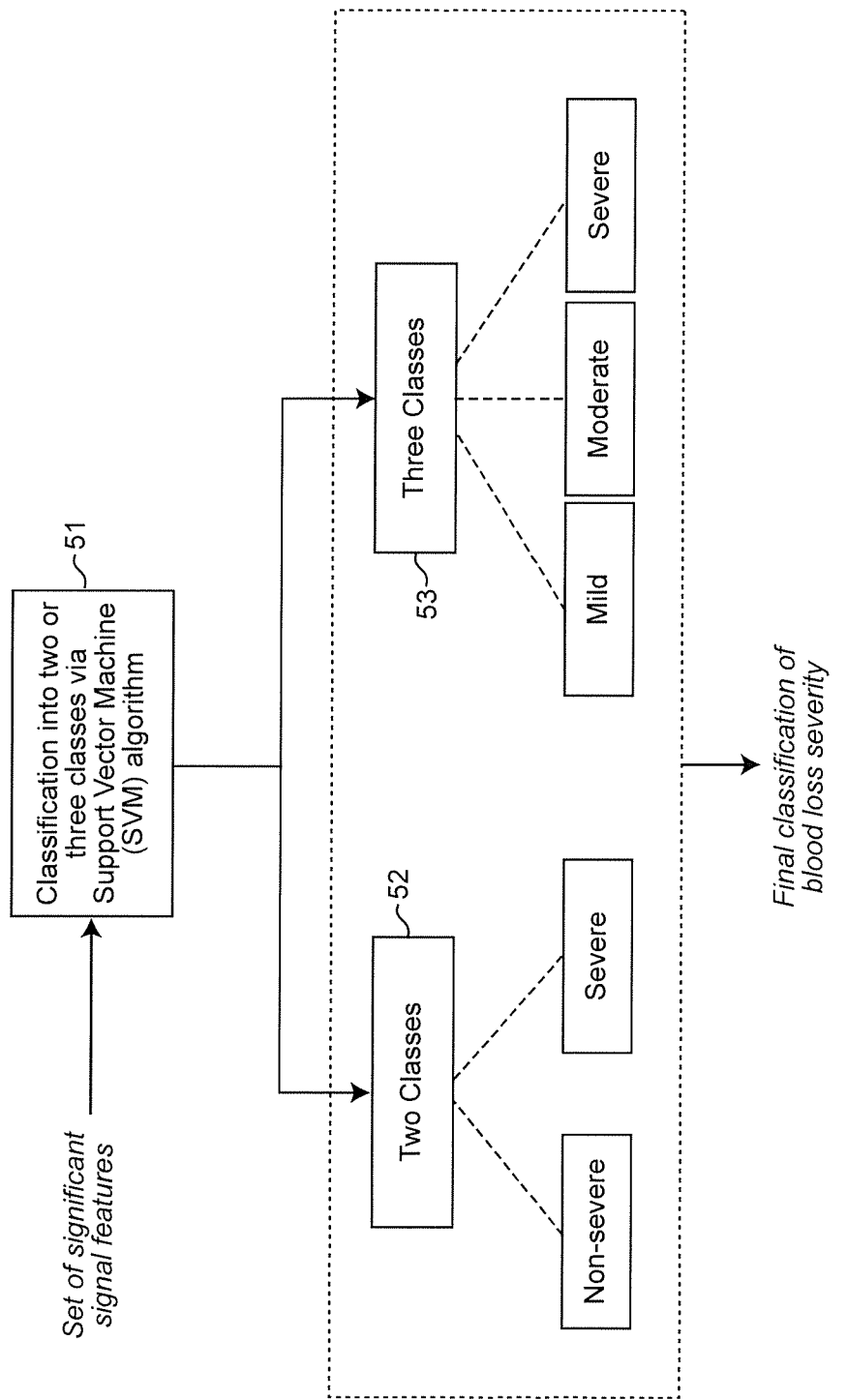
FIG. 5 is a flowchart illustrating the logic of the hypovolemia severity prediction via machine learning component of the process shown in FIG. 2.

FIG. 5 is a flowchart explaining classification process. This stage provides hypovolemia severity prediction via machine learning. This stage takes as input the filtered feature set generated in the preceding stage and applies machine learning, specifically, via Support Vector Machine (SVM), to generate a predictive model for hypovolemia severity. Note that this section requires prior training of the predictive model; the model is then deployed in a real-world environment for real-time prediction of hypovolemia severity for new patients. This is done by collecting TCD and ECG signals from the new patient, performing the analysis process described in the preceding stages (which is done automatically and rapidly), then feeding the resulting features into the predictive model to gain a final classification of blood loss severity.

The input to this stage is the set of significant features extracted from TCD and ECG signals of patient. The first step 51 is classification via Support Vector Machine (SVM). SVM is a machine learning technique used primarily for classification. It is a supervised method, meaning that, given a training set of example cases labeled with categories, it constructs a model that predicts the most suitable category for a new, unlabeled example. In a mathematical sense, SVM constructs a hyperplane in high-dimensional space which best preserves separation between the various categories (classes). Each of the examples is treated as a data-point in this high-dimensional space, so the optimal hyperplane can be considered as the one that divides the classes by as wide a gap as possible. Essentially, it is based on the distance between data-points. Since SVM performs well on complex data (where many features are used for prediction), it has been successfully used in solving many real world problems such as protein analysis, cancer data classification, and hand-writing recognition.

SVM was chosen for the system following experimental tests using two other machine learning algorithms: C4.5 (a decision-tree method) and AdaBoost (which combines multiple predictive models to improve accuracy). SVM offered the highest performance in these tests. However, due to the modular nature of the system embodiment, where the predictive model is generated prior to deployment, it is simple to switch methods depending on the prediction task. For more detail on the SVM algorithm, see *The Nature of Statistical Learning Theory* (Vladimir N. Vapnik, Springer-Verlag, 1995).

Steps 52 and 53 separates the outputs of step 1 into two or three classes, respectively. A patient's hypovolemic state can be classified into either two or three classes, depending on the needs of the medical personnel using the system. The two-class option, step 52, simply divides patients into two groups: severe level of hypovolemia, or non-severe. The three-class option, step 53, offers a more refined prediction: mild, moderate, or severe level. Whichever option is chosen, the final output of the system for a new patient is a single classification label predicting their level of severity of hypovolemia. This is generated in real-time and can thus be highly valuable to medical personnel in deciding the urgency of treatment and which methods may be most suited to the individual case.

Figure 6:
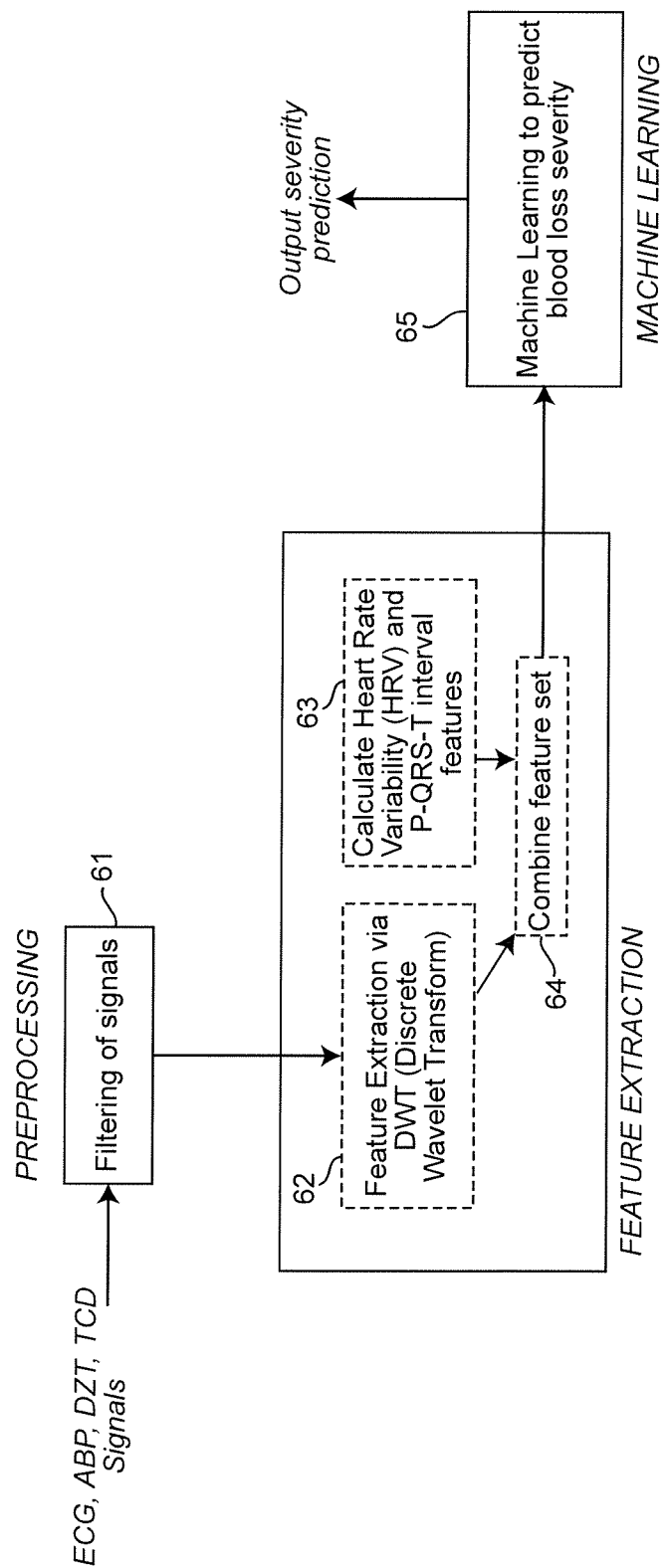
FIG. 6 is a flowchart illustrating the overall logic implemented integrating four physiological signals to detect the severity of hypovolemia.

As previously mentioned, the embodiment of the invention has two applications, described as Application 1 and Application 2, where Application 2 is an extension of Application 1. In Application 2, multiple physiological signals (ECG, arterial blood pressure (ABP), impedance (DZT), and TCD) are integrated to detect the severity of hypovolemia. FIG. 6 presents an overview of this application and the function that each component serves, with references to more detailed diagrams. The first step 61 is preprocessing of physiological signals. The inputs are ECG ABP, DZT, and TCD signals. The next stage is feature extraction. This is done in step 62 using Discrete Wavelet Transform (DWT). In step 63, heart rate variability (HRV) and P-QRS-T interval features are calculated. The outputs of steps 62 and 63 are combined in step 64 to generate a combined feature set. This combined feature set is input to the machine learning step 65 to predict blood loss severity.

Figure 7:
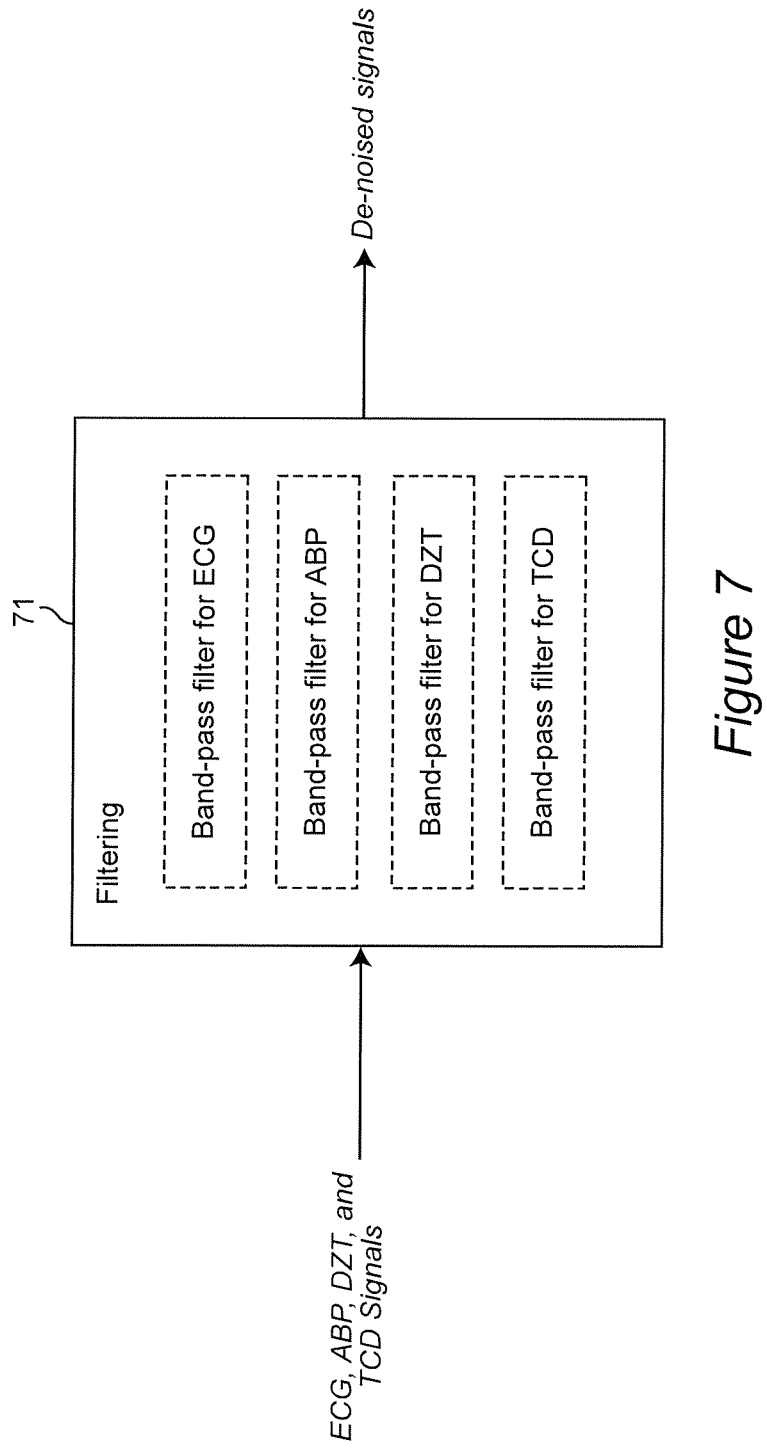
FIG. 7 is a flowchart illustrating the pre-processing component of the process shown in FIG. 6.

Step 61, filtering of signals, is illustrated in more detail in FIG. 7. This stage applies filtering to the raw input signals to remove noise prior to processing. The inputs to this stage are four physiological signals: electrocardiogram (ECG), arterial blood pressure (ABP), impedance (DZT), and Transcranial Doppler (TCD). The outputs are de-noised versions of the input signals.

Transcranial Doppler (TCD) and electrocardiogram (ECG) have been defined above. In this application, two additional signals are added: DZT is a signal measuring thoracic electrical bio-impedance, collected via electrodes attached to the patient, while arterial blood pressure (ABP) measures the force exerted on the walls of blood vessels by circulating blood. Physiological signals are susceptible to noise during their collection, due to factors such as patient movement and power line interference. Therefore, stage 71 performs band-pass filtering to remove this noise. An order 2 band-pass filter is applied to all signals separately. This attenuates all frequencies in the signal that fall outside a specified range, decided in advance based on the dominant frequency of the signal.

Figure 8:
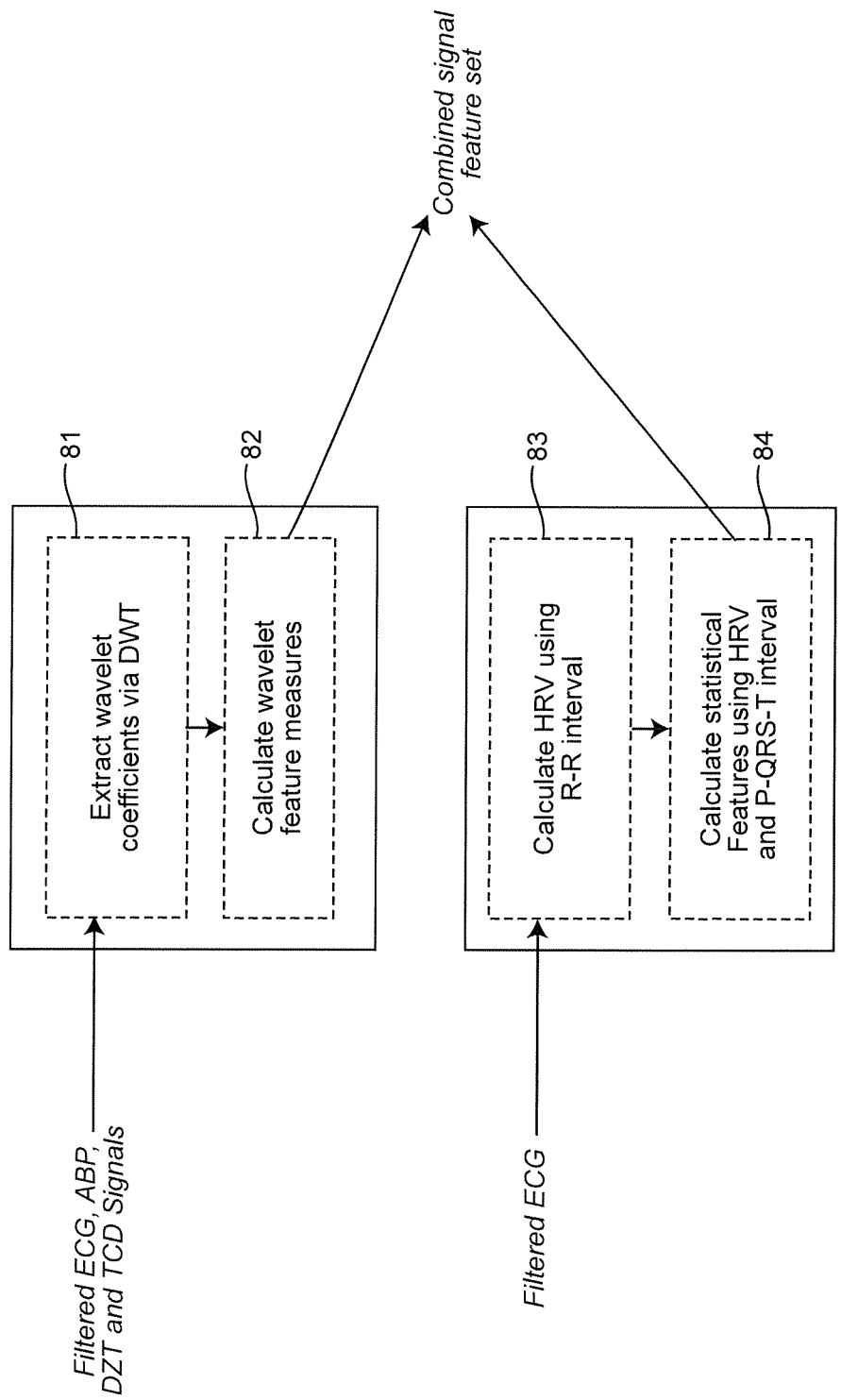
FIG. 8 is a flowchart illustrating the logic of the feature extraction component of the process shown in FIG. 6.

FIG. 8 shows in more detail the feature extraction step 62 shown in FIG. 6. This stage extracts key features from the filtered physiological signals via wavelet transform and HRV analysis. The inputs to this stage are the four filtered physiological signals (ECG, ABP, DZT, and TCD). The output is a set of quantitative features extracted from these signals using the discrete wavelet transform (DWT) and heart rate variability (HRV) analysis.

In step 81, wavelet decomposition of the signals (ECG, ABP, DZT, and TCD) is performed. Signal decomposition is performed using the discrete wavelet transform (DWT) with the Daubechies 4 (db4) mother wavelet. The signals are decomposed to four levels using a 40-second non-overlapping sliding window. Note that recent tests have found that eight levels may offer improved performance; however, since the parameters of the approach are easily altered, this does not affect the methodology itself.

This step applies a sliding window as part of the decomposition process. This divides the signal into non-overlapping samples of a specified length (here, 40 seconds). DWT is applied to each of these windows. This allows a finer degree of detail to be captured from the signal, particularly the rapid changes that can occur depending on patient state. This window size can be altered as needed. The output of this step is a set of detail coefficients at four levels ($D_1$, $D_2$, $D_3$, $D_4$) and an approximation coefficient A.

In step 82, calculation of wavelet features is performed. Several key quantitative features are calculated using the coefficients extracted in the previous step. These are as follows:

$$\sigma_D^j = \sqrt{\frac{1}{n}\sum_{i=1}^{n}(d_i^j - \mu^j)^2}$$

($\sigma_D^j$=standard deviation of detail coefficients at level j)

$$\sigma_A = \sqrt{\frac{1}{n}\sum_{i=1}^{n}(a_i - \mu_a)^2}$$

($\sigma_A$=standard deviation of approximation coefficient)

$$(E_D^j) = \sum_{i=1}^{n}(d_i^j)^2$$

($E_D^j$=energy of detail coefficients at level j)

$$(E_A) = \sum_{i=1}^{n}(a_i)^2$$

($E_A$=energy of approximation coefficient)

where n and m are the lengths of the detail coefficients and the approximation coefficient respectively, $d_i^j$ is the detail coefficient of level j, $a_i$ is the approximation coefficient, $\mu^j$ is the mean of the detail coefficients at level j, and $\mu_a$ is the mean of the approximation coefficient.

At Steps 83 and 84, Statistical Features are Calculated Using Heart Rate Variability (HRV) and P-QRS-T interval. A typical ECG signal consists of a P wave, a QRS complex and a T wave. The P wave and QRS represent atrial and ventricular depolarization, respectively, while the T wave characterizes the subsequent rapid re-polarization of the ventricles. To extract useful knowledge from the ECG signal, the system first identifies the P-QRS-T intervals. After detection, the PQ, QS, PR, ST and QT intervals are considered separately. The duration of each interval type is analyzed and used to calculate the following features: standard deviation, mean, median, minimum, and maximum duration. These features are calculated using non-overlapping sliding windows of 40 seconds length.

Heart rate variability (HRV) is a measure of variation in heart rate in a beat-to-beat interval, and is in widespread clinical use as a measure of cardiovascular state. In order to measure the beat-to-beat interval, the R-wave in the ECG must first be identified. This allows calculation of the R-R interval, defined as the time duration between two consecutive R waves in the ECG. An HRV series is constructed by measuring the variation of successive R-R intervals; this can be used to calculate various metrics that characterize the HRV.

Figure 9:
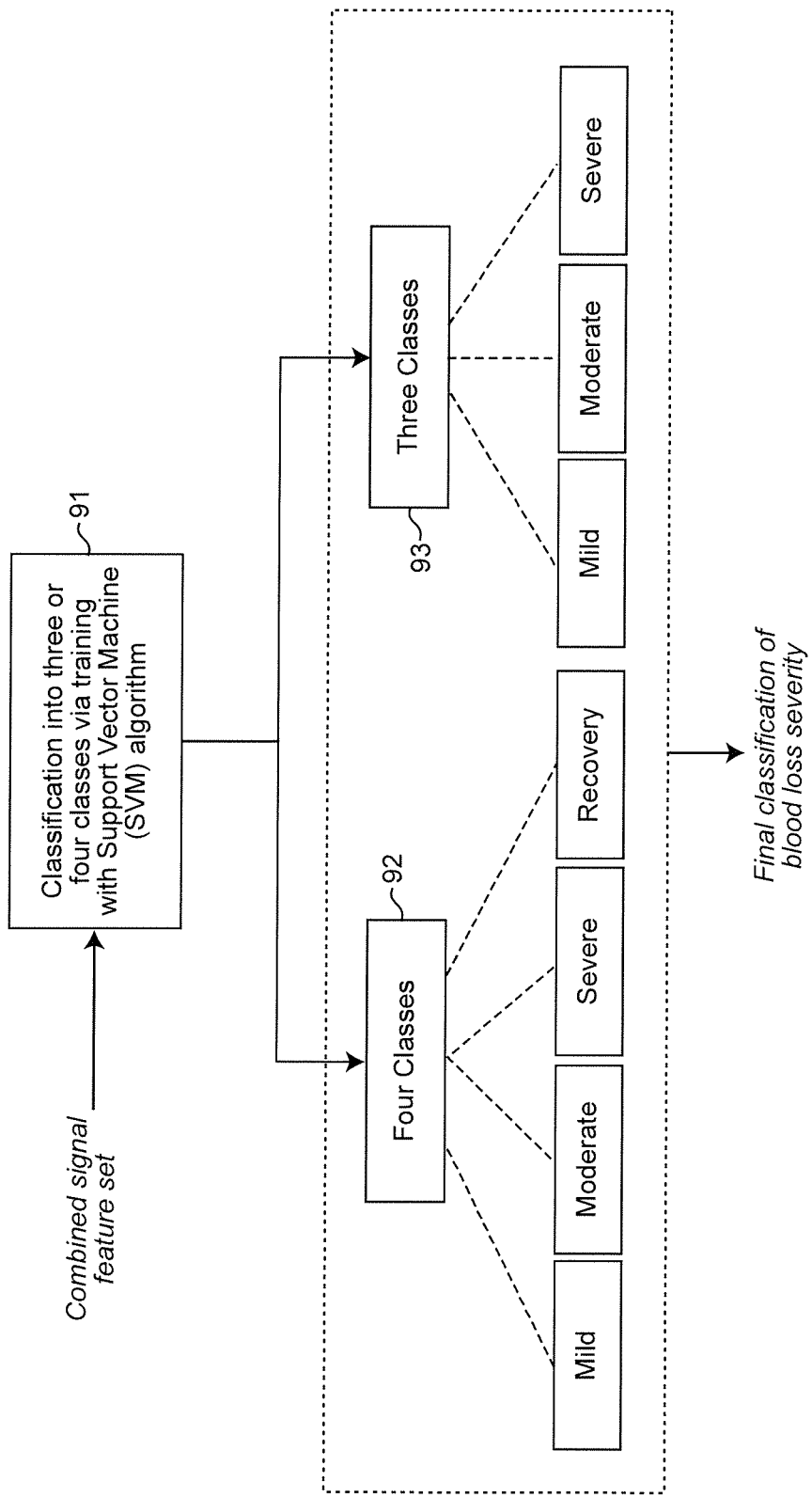
FIG. 9 is a flowchart illustrating the logic of the hypovolemia severity prediction via machine learning component of the process shown in FIG. 6.

Hypovolemia severity prediction via machine learning, step 63 in FIG. 6, is illustrated in more detail in FIG. 9. This stage takes as input the filtered feature set generated in the preceding stage and applies machine learning via Support Vector Machine (SVM) to generate a predictive model for hypovolemia severity. As with Application 1, this stage requires prior training of the predictive model before it is deployed in a real-world environment to be used in real-time prediction for new patients. The TCD, ECG, DZT and ABP signals are collected from the new patient and analyzed using the process described above, with the resulting features being fed into the predictive model to classify the new patient's degree of hypovolemia.

The inputs to this stage are a set of significant features extracted from TCD, DZT, ABP and ECG signals of patient, along with HRV and P-QRS-T interval information. The output of this stage is a prediction of the severity of hypovolemia—either as one of three classes (mild, moderate, and severe), or as one of four (mild, moderate, severe, and recovery).

At step 91, classification via Support Vector Machine (SVM) is performed. This stage uses essentially the same process as in FIG. 5 of Application 1; details on the construction of the predictive model can be found there. The methodology is the same, and is simply applied to a larger input feature set with more output classes. Note that the training set used to construct the model must include as many of the extracted features as possible for each case.

Steps 92 and 93 perform separation into three or four classes, respectively. In this application, a new patient's hypovolemic state is classified into either three or four classes, depending on the needs of the medical personnel using the system. The three-class option divides patients into the following groups based on their level of hypovolemia: mild, moderate, or severe. The four-class option includes an addition "recovery" group, which indicates that the patient's state is returning to their baseline. This has additional utility in analyzing the effectiveness of difference treatments for hypovolemia, in terms of how quickly a patient's condition returns to normal after the treatment is applied.

As in the first application, the final output of the system for a new patient is a single classification label predicting their level of severity of hypovolemia, generated in real-time using the collected signals.

While the invention has been described in terms of a single preferred embodiment with multiple applications, those skilled in the art will recognize that the invention can be practiced with modification within the spirit and scope of the appended claims.

Having thus described our invention, what we claim as new and desire to secure by Letters Patent is as follows:

1. A real-time decision-support system for predicting hemorrhagic shock of a patient comprising:
    means for receiving electrocardiogram (ECG) signals from the patient;
    means for receiving transcranial Doppler (TCD) signals from the patient;
    first bandpass filter for filtering the ECG signals;
    second bandpass filter for filtering the TCD signals;
    first means using Discrete Wavelet Transform (DWT) to decompose filtered ECG signals to generate a first set of wavelet coefficients and selecting significant signal features from the first set of wavelet coefficients;
    second means using DWT to decompose filtered TCD signals to generate a second set of wavelet coefficients and selecting significant signal features from the second set of wavelength coefficients;
    data processing means receiving significant signal features and, using machine learning, evaluating and classifying hypovolemia severity based on the selected significant signal features generated from the wavelet coefficients of input ECG and TCD signals from the patient; and
    a display for displaying a classification of blood loss severity.

2. The real-time decision-support system according to claim 1, wherein the first and second means using DWT uses the Daubechies 4 (db4) form of DWT.

3. The real-time decision-support system according to claim 1, wherein the data processing means extracts features for hypovolemia severity prediction from TCD and ECG signals using statistical calculations and significance testing.

4. The real-time decision-support system according to claim 1, wherein the data processing means uses support vector machine (SVM) to generate a predictive model for hypovolemia severity.

5. The real-time decision-support system according to claim 1, further comprising:
    means for generating arterial blood pressure (APB) signals from the patient; and
    means for generating thoracic electrical bio-impedance (DZT) signals from the patient;
    and wherein the data processing means extracts features for hypovolemia severity prediction from APB and DZT signals as well as TCD and ECG signals using statistical calculations and significance testing.

6. A computer implemented real-time decision-support method for predicting hemorrhagic shock of a patient, comprising the steps of:
    receiving electrocardiogram (ECG) and transcranial Doppler (TCD) signals from the patient;
    decomposing the ECG and TCD signals by a computer using discrete wavelet transformation (DWT) to generate a first set of wavelet coefficients for the ECG and selecting significant signal features from the wavelet coefficients of the ECG signals and to generate a second set of wavelet coefficients for the TCD and selecting significant signal features from the wavelet coefficients of the TCD signals;
    combining by a computer wavelet coefficients into a raw feature set;
    extracting by a computer statistical features from the raw feature set to produce a new feature set;
    testing a significance of each new feature in the new feature set;
    applying machine learning to new features derived from significant features for classification based on said testing step; and
    displaying a prediction of blood loss severity.

7. The computer implemented real-time decision support method according to claim 6, wherein prior to the step of decomposing the ECG and TCD signals, filtering the ECG and TCD signals to eliminate noise from the signals.

8. The computer implemented real-time decision support method according to claim 6, wherein the step of extracting statistical features is done via analysis of variance (ANOVA) to generate a set of significant signal features.

9. The computer implemented real-time decision support method according to claim 6, wherein the step of applying machine learning to significant features is via Support Vector Machine (SVM) to generate a predictive model for hypovolemia severity.

10. The computer implemented real-time decision support method according to claim 6, further comprising the step of receiving Arterial Blood Pressure (ABP) and thoracic electrical bio-impedance (DZT) signals from the patient, wherein the step of decomposing includes decomposing the ABP and DZT signals using discrete wavelet transform (DWT) to generate a third set of wavelet coefficients and selecting significant signal features from the ABP signals and to generate a fourth set of wavelet coefficients and selecting significant signal features from the DZT signals.

* * * * *

UNITED STATES PATENT AND TRADEMARK OFFICE
CERTIFICATE OF CORRECTION

PATENT NO. : 8,762,308 B2
APPLICATION NO. : 13/255549
DATED : June 24, 2014
INVENTOR(S) : K. Najarian et al.

It is certified that error appears in the above-identified patent and that said Letters Patent is hereby corrected as shown below:

In the Specification

At Column 1, delete lines 8-11 and insert the following:

--This invention was made with government support under contract number W81XWH-06-0472 awarded by the USAMRMC. The government has certain rights in the invention.--

Signed and Sealed this
Seventh Day of October, 2014

Michelle K. Lee
*Deputy Director of the United States Patent and Trademark Office*